United States Patent [19]

Arcusin et al.

[11] Patent Number: 5,312,369

[45] Date of Patent: May 17, 1994

[54] SAFETY HOOD FOR HYPODERMIC NEEDLES

[76] Inventors: Carlos E. Arcusin; Ruben A. Makuc, both of San Nicolas 274, Buenos Aires, Argentina

[21] Appl. No.: 97,592

[22] Filed: Jul. 26, 1993

Related U.S. Application Data

[63] Continuation of Ser. No. 802,143, Dec. 3, 1991, abandoned.

[30] Foreign Application Priority Data

Dec. 4, 1990 [AR] Argentina ............................ 318.520

[51] Int. Cl.$^5$ .................................................. A61M 5/32
[52] U.S. Cl. ................................... 604/192; 604/198; 604/263
[58] Field of Search ............... 604/192, 263, 110, 187, 604/218, 195, 197, 198, 199; 128/919; 206/364, 365, 366

[56] References Cited

U.S. PATENT DOCUMENTS

| | | | |
|---|---|---|---|
| 3,658,061 | 4/1972 | Hall | 604/263 |
| 4,664,259 | 5/1987 | Landis | 206/365 |
| 4,820,277 | 4/1989 | Morelli | 604/192 |
| 4,838,871 | 6/1989 | Luther | 604/192 |
| 4,883,469 | 11/1989 | Glazier | 604/192 |
| 4,976,699 | 12/1990 | Gold | 604/192 |
| 4,982,842 | 1/1991 | Hollister | 206/365 |
| 5,017,189 | 5/1991 | Boumendil | 604/192 |
| 5,055,102 | 10/1991 | Sitaik | 604/192 |
| 5,151,089 | 9/1992 | Kirk et al. | 604/192 |
| 5,232,455 | 8/1993 | Hollister | 604/192 |

FOREIGN PATENT DOCUMENTS

| | | | |
|---|---|---|---|
| 2618685 | 2/1989 | France | 604/263 |
| 7162 | 12/1987 | World Int. Prop. O. | 604/263 |
| 9001348 | 2/1990 | World Int. Prop. O. | 604/263 |

*Primary Examiner*—C. Fred Rosenbaum
*Assistant Examiner*—Vanitha Alexander
*Attorney, Agent, or Firm*—Michael J. Striker

[57] ABSTRACT

A safety hood for hypodermic needles has an elongated body having a U-shaped cross-section and two ends spaced from one another in a direction of elongation with one of the ends being closed, elements for preventing undesired withdrawal of a needle from the hood provided in the body, and a pivot member provided on another of the ends and formed so that the body can be turned in a direction transverse to its direction of elongation between a first position in which the body surrounds and closes the needle and a second position in which the body is turned away from the needle and exposes the needle.

9 Claims, 1 Drawing Sheet

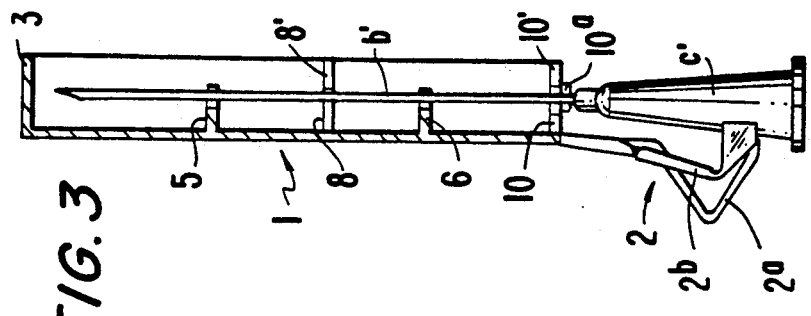
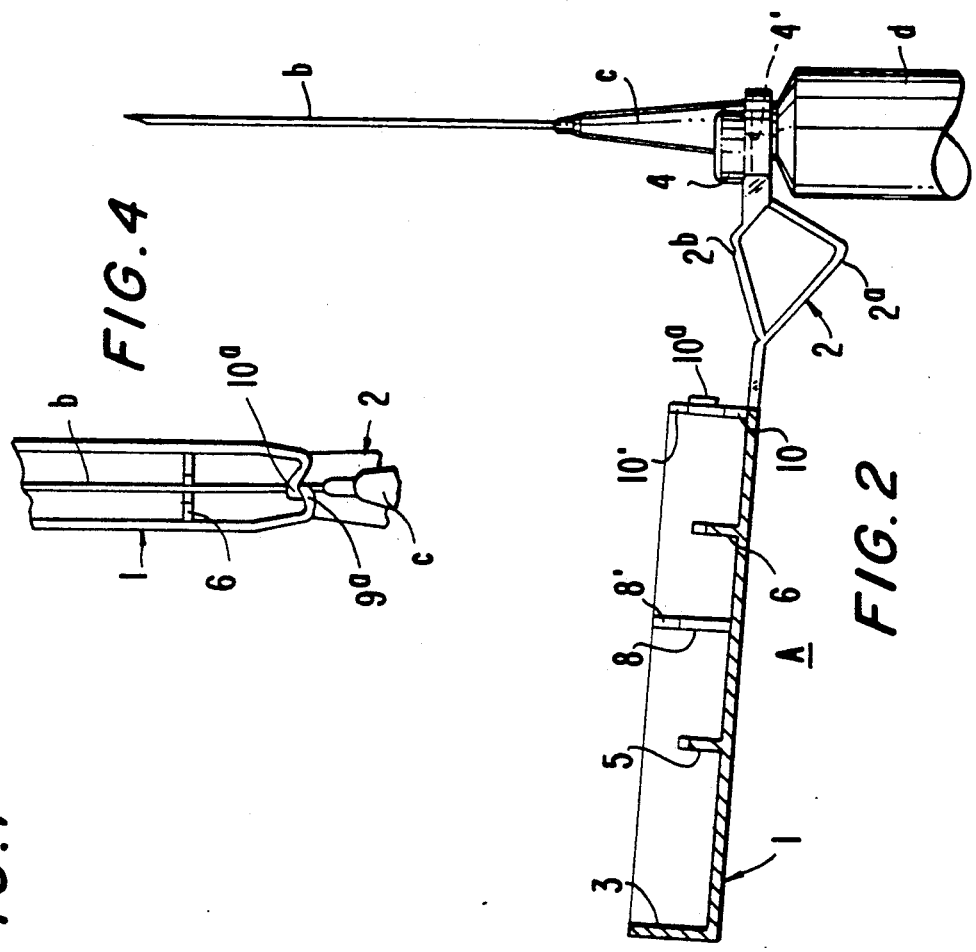
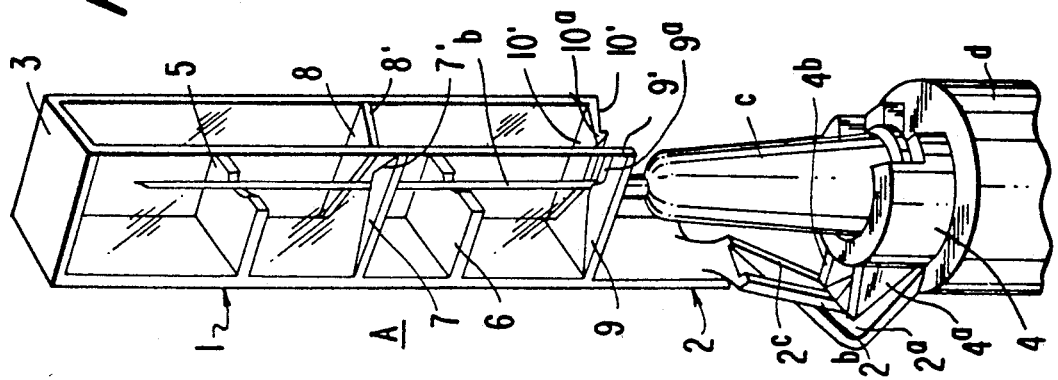

SAFETY HOOD FOR HYPODERMIC NEEDLES

This application is a continuation of application Ser. No. 802,143, filed Dec. 3, 1990, now abandoned.

BACKGROUND OF THE INVENTION

This invention refers to a safety hood for hypodermic needles. More particularly it relates to a safety hood which is designed for preventing accidental pricking of a user by a needle.

Generally, as it is known the administration of injections and blood extraction involves using syringes that, both if they are reusable or non reusable, are provided with corresponding needles carrying a removeable hood. The hood protects the needles and constitutes a safety means against the possibility of accidental pricking of the operator.

The thusly achieved safety is not complete and the possibility of accidental pricking remains as the replacing or removing of the hood is made along the length of the needle.

Presently, because of the risk of infected through blood contact with diseases like AIDS and hepatitis, the use of the hood would unavoidable be—due to the above reasons—not completely safe. Considering that a health professional may operate 300 injections or blood extractions per month and that HIV carriers and AIDS patients can be estimated to represent 0.3% of the population, a few accidental prickings mean an unacceptable risk.

SUMMARY OF THE INVENTION

The problem discussed above made us think that the way to solve it is related with providing a hood that can be laterally removed or installed and that the installing can be made before or after the injection or blood extraction with similar efficiency. This installation after use can be made using an adaptable member between the syringe nozzle and the needle socket or, when after use making said member integral with said socket where the syringe nozzle is inserted. There should exist a pivot relationship between said hood and said adaptable member designed to allow said lateral insertion or removal of said hood under pressure, and in said second case, after releasing the lock provided by a pair of lock lugs which ensure that said needle remains in said hood.

Said safety hood, designed to overcome the problem mentioned above, consists of a flexible body of "U" cross section having its free end closed and provided in the opposite end with a pivot member originating in its normal wall and having an integral conventional spring or "flip-flop" ending in an adapter member, and its body carrying in the inside thereof, from said closed end, at least one needle stop and one vise-wall having a V cut to guide said needle, as well as a pair of locking lugs integral with the hood body and also having C cuts and representing means to oppose an undesired exit of the needle contained therein.

This invention can be practiced using any sizes, materials and forms deemed convenient for its ends.

In order to make easier the understanding and practice of this patent, now it will be described in detail with reference to the illustrative drawings attached hereto.

BRIEF DESCRIPTION OF THE DRAWING

FIG. 1 is a perspective view of the hood of the present invention, according to the preferred embodiment and mounted on syringe carrying a hypodermic needle.

FIG. 2 is a longitudinal section of the assembly of FIG. 1 with said hood pivoted to the side of the said hypodermic needle.

FIG. 3 is a longitudinal section of an alternate embodiment of the present invention.

FIG. 4 is a partial front elevation of said hood showing the locking lugs for said hypodermic needle.

In all these figures, the same reference numerals design the same or corresponding parts.

DESCRIPTION OF THE PREFERRED EMBODIMENTS

According to the preferred embodiment shown in FIGS. 1 and 2, the safety hood a for hypodermic needles, such as that designated by b having a conical base c and mounted on the nozzle of a conventional syringe d, has of a flexible body 1 with a pivot member 2, opposed to its free closed end 3 and connected to an adapter member 4.

The body 1 has a "U" cross section and contains a pair of needle bearings 5 and 6, and a vise wall having parts 7 and 8 with oblique cuttings 7' and 8' defining an entrance guide for said needle. It also has a pair of co-planar locking lugs 9 and 10 which, besides having similar oblique cuttings 9' and 10' with the same purpose than those of the vise-wall, are provided with respective projections 9a and 10a capable of locking under manual pressure and thus apt to avoid the undesired escape of the needle b from the safety hood a of this invention.

The pivot member 2 projects from the longitudinal wall of body 1 and has a first solid section and a second section comprising an integral spring or "flip-flop" defined by an angle branch 2a in an intermediate position between side pivoting branches 2b and 2c resiliently connected to the solid section and to the adapter member 4. The last connection is direct in the case of the angle branch or spring 2a, and in the case of the branches 2b and 2c to respective lugs 4a and 2b integral with the adapter member 4 which has a body with incomplete angular cross section and is provided with the inner shoulder 4'.

In the embodiment shown in FIG. 3 the adaptor member 4 has been dispensed with and, therefore, the safety hood a of this invention is connected through its pivot member 2 to the base c' of the needle b'. In this case, as the flip-flop pivot is centered on the needle base, the assembly may be used with any syringe nozzle, including those known as "twist off".

The safety good a of this invention can be installed before or after use from the side by first mounting the adapter member 4 between the beginning of the conventional syringe nozzle d and the base c of the hypodermic needle b; then pressing manually the body 1 against any firm surface to cause the installation thereof on the needle c abutting against bearings 5 and 6 and through the vise-wall between its parts 7 and 8 having end lugs 9 and 10; and finally once the needle has been used causing the interlocking of the end lugs 9 and 10 by means of the projections 9a and 10a so as to avoid an undesired escape of said needle. During the normal use, the hood is in a pivoted position and secured by the flip-flop 2a where it does not interfere with the operation, and after use a simple hand pressure activates the flip-flop spring and the hood moves to its rest position covering the needle.

The safety hood of this invention can be installed or removed as an assembly consisting of the needle b and the safety hood a and, in this case, with the needle base c inserted into the adapter member 4 and abutting against its inner should 4c.

The same happens in the case of the embodiment of FIG. 3 where the body 1 of said safety hood a is integral with base c' of needle b'.

It will be understood that each of the elements described above, or two or more together, may also find a useful application in other types of constructions differing from the types described above.

While the invention has been illustrated and described as embodied in a safety hood for hypodermic needles, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A safety hood for hypodermic needles, comprising an elongated body having a U-shaped cross-section formed to surround and enclose a needle and two ends spaced from one another in a direction of elongation, one of said ends being closed; means for preventing undesired withdrawal of a needle from said hood, provided in said body; and a pivot member provided on another of said ends, said pivot member being connected to said body and connectable to the needle and including a springy flip-flop element formed so that said body can be turned in a direction transverse to its direction of elongation between a first position in which said body surrounds and closes the needle and a second position in which said body is turned away from the needle and exposes the needle, said pivot member having a first solid portion and a second portion having lateral arms and a central angular arm which together form a flip-flop spring with said arms resiliently joined to said solid portion.

2. A safety hood as defined in claim 1, wherein said body is provided with at least one needle bearing.

3. A safety hood as defined in claim 1, wherein said body is provided with a vise-wall having parts provided with oblique cuttings for guiding the needle during its insertion.

4. A safety hood as defined in claim 1, wherein said preventing means includes a pair of locking lugs projecting from said body and having oblique guide cuttings.

5. A safety hood as defined in claim 4, wherein said lugs are coplanar.

6. A safety hood as defined in claim 1; and further comprising an adaptor member having an adaptor body for mounting between a base of a syringe nozzle and a needle base, said adaptor member having a stop shoulder in its interior.

7. A safety hood as defined in claim 6, wherein said adaptor member is integral with said needle base.

8. A safety hood for hypodermic needles, comprising an elongated body having a U-shaped cross-section formed to surround and enclose a needle and two ends spaced from one another in a direction of elongation, one of said ends being closed; means for preventing undesired withdrawal of a needle from said hood, provided in said body; a pivot member provided on another of said ends, said pivot member being connected to said body and connectable to the needle and including a springy flip-flop element formed so that said body can be turned in a direction transverse to its direction of elongation between a first position in which said body surrounds and closes the needle and a second position in which said body is turned away from the needle and exposes the needle, said body being provided with at least one needle bearing and a vise-wall having parts with oblique cuttings for guiding the needle during its insertion, said preventing means including a pair of locking lugs projecting from said body and having oblique guide cuttings, said lugs having end formations providing a locking closure of the needle and formed as end projections shaped as teeth, said pivot member having a first solid portion and a second portion having lateral arms and a central angular arm which together form a flip-flop spring and are resiliently joined to said solid portion; and an adapter member with an adaptor body for mounting between a base of a syringe nozzle and a needle base and having a stop shoulder in its interior.

9. A safety hood for hypodermic needles, comprising an elongated body having a U-shaped cross-section formed to surround and enclose a needle and two ends spaced from one another in a direction of elongation, one of said ends being closed; means for preventing undesired withdrawal of a needle from said hood, provided in said body; and a pivot member provided on another of said ends, said pivot member being connected to said body and connectable to the needle and including a springy flip-flop element formed so that said body can be turned in a direction transverse to its direction of elongation between a first position in which said body surrounds and closes the needle and a second position in which said body is turned away from the needle and exposes the needle, said preventing means including a pair of locking lugs projecting from said body and having end formations which provide a locking closure of the needle and are formed as teeth.

* * * * *